(12) United States Patent
Shibuya et al.

(10) Patent No.: US 8,282,946 B2
(45) Date of Patent: Oct. 9, 2012

(54) WATER-SOLUBLE GINGER ROOT EXTRACT

(75) Inventors: Yusuke Shibuya, Haga-gun (JP);
Shigeru Moriwaki, Haga-gun (JP);
Naoko Tsuji, Haga-gun (JP)

(73) Assignee: Kao Corporaion, Tokyo (JP)

( * ) Notice: Subject to any disclaimer, the term of this patent is extended or adjusted under 35 U.S.C. 154(b) by 1806 days.

(21) Appl. No.: 11/246,218

(22) Filed: Oct. 11, 2005

(65) Prior Publication Data
US 2006/0099280 A1    May 11, 2006

Related U.S. Application Data

(62) Division of application No. 10/209,858, filed on Aug. 2, 2002, now abandoned.

(30) Foreign Application Priority Data

Aug. 3, 2001  (JP) .................................. 2001-236854

(51) Int. Cl.
*A61K 8/02* (2006.01)
*A61K 8/64* (2006.01)
*A61K 8/65* (2006.01)
*A61K 8/97* (2006.01)
*A61K 36/8962* (2006.01)
*A61Q 5/00* (2006.01)
*A61Q 9/00* (2006.01)
*A01N 65/00* (2009.01)

(52) U.S. Cl. ........ 424/401; 424/70.14; 424/74; 424/756
(58) Field of Classification Search .................. 424/401, 424/70.14, 74, 756
See application file for complete search history.

(56) References Cited

U.S. PATENT DOCUMENTS

| | | | |
|---|---|---|---|
| 4,013,788 A * | 3/1977 | Jolles et al. ................. | 424/282.1 |
| 4,720,489 A | 1/1988 | Shander | |
| 5,095,007 A | 3/1992 | Ahluwalia | |
| 5,096,911 A | 3/1992 | Ahluwalia et al. | |
| 5,132,293 A | 7/1992 | Shander et al. | |
| 5,143,925 A | 9/1992 | Shander et al. | |
| 5,190,757 A | 3/1993 | Kim | |
| 5,218,125 A | 6/1993 | Chen et al. | |
| 5,252,604 A | 10/1993 | Nagy et al. | |
| 5,364,885 A | 11/1994 | Ahluwalia et al. | |
| 5,411,991 A | 5/1995 | Shander et al. | |
| 5,444,090 A | 8/1995 | Ahluwalia | |
| 5,455,234 A | 10/1995 | Ahluwalia et al. | |
| 5,468,476 A | 11/1995 | Ahluwalia et al. | |
| 5,474,763 A | 12/1995 | Shander et al. | |
| 5,554,608 A | 9/1996 | Ahluwalia et al. | |
| 5,648,394 A * | 7/1997 | Boxall et al. ................. | 514/567 |
| 5,652,273 A | 7/1997 | Henry et al. | |
| 5,674,477 A | 10/1997 | Ahluwalia | |
| 5,728,736 A | 3/1998 | Shander et al. | |
| 5,776,442 A | 7/1998 | Ahluwalia | |
| 5,824,665 A | 10/1998 | Henry et al. | |
| 5,840,752 A | 11/1998 | Henry et al. | |
| 5,908,867 A | 6/1999 | Henry et al. | |
| 5,939,458 A | 8/1999 | Henry et al. | |
| 5,958,946 A | 9/1999 | Styczynski et al. | |
| 5,962,466 A | 10/1999 | Styczynski et al. | |
| 5,968,488 A | 10/1999 | Wachter et al. | |
| 6,020,006 A * | 2/2000 | Styczynski et al. ........... | 424/646 |
| 6,037,326 A | 3/2000 | Styczynski et al. | |
| 6,060,471 A | 5/2000 | Styczynski et al. | |
| 6,063,381 A * | 5/2000 | Staggs .......................... | 424/734 |
| 6,093,748 A | 7/2000 | Ahluwalia et al. | |
| 6,171,595 B1 | 1/2001 | Suzuki et al. | |
| 6,218,435 B1 | 4/2001 | Henry et al. | |
| 6,239,170 B1 | 5/2001 | Ahluwalia et al. | |
| 6,248,751 B1 | 6/2001 | Ahluwalia et al. | |
| 6,264,928 B1 | 7/2001 | Jean et al. | |
| 6,375,948 B1 | 4/2002 | Tsuji et al. | |
| 6,391,346 B1 | 5/2002 | Newmark et al. | |
| 2003/0012755 A1 * | 1/2003 | Styczynski et al. ........... | 424/70.1 |

FOREIGN PATENT DOCUMENTS

| | | |
|---|---|---|
| EP | 1 051 965 | 11/2000 |
| JP | 60-181007 | 9/1985 |
| JP | 61-050909 | 9/1991 |
| JP | 04-182479 | 6/1992 |
| JP | 6-239736 | 8/1994 |
| JP | 11-10632 | 4/1999 |
| JP | 11-106321 | 4/1999 |
| WO | WO 96/10387 | 4/1996 |

OTHER PUBLICATIONS

Nakumura et al. Mutagen and anti-mutagen in ginger, *Zingiber officinale*, Mutation Research, 103, 1982, 119-126.*
Beek et al. "Investigation of the essential oil of Vietnamese ginger", Phytochemistry, 1987, vol. 26, No. 11, pp. 3005-3010.*
Chen et al. "Volatile Compounds in Ginger Oil Generated by Thermal Treatment", published Oct. 3, 1989.*
Rogers, J.A. "Advances in Spice Flavor and Oleoresin", published Jan. 1, 1969.*
Yoshihiro Kano, "Natural Medicine", Feb. 20, 1986, 40, pp. 333-339.
H. Nakamura, et al., Mutation Research, vol. 103, pp. 119-126, XP-009001392, "Mutagen and Anti-Mutagen in Ginger, *Zingiber officinale*", 1982.
Derwent Abstract, AN 1994-313611, XP-002221495, JP 06-239736, Aug. 30, 1994.
Patent Abstracts of Japan, JP 11-106321, Apr. 20, 1999.
Katiyar et al. (Inhibition of tumor promotion in SENCAR mouse skin by ethanol extract of *Zingiber officinale* rhizome, Cancer Research Mar. 1, 1996; 56(5):1023-30).
Inhibitory action of natural food components on the formation of carcinogenic nitrosamine, Bulletin of Korean Fisheries Society 1993, 26 (4): 289-295.
Office Action issued Feb. 22, 2011 in Japanese Patent Application No. 2001-236854 (with English translation).

* cited by examiner

*Primary Examiner* — Richard Schnizer
*Assistant Examiner* — Audrea Buckley
(74) *Attorney, Agent, or Firm* — Oblon, Spivak, McClelland, Maier & Neustadt, L.L.P.

(57) ABSTRACT

Provided are a water-soluble ginger root extract which is a water extract or a hydrous alcohol extract of a ginger root and is substantially free of gingerols; and a hair growth inhibitor and a preparation for external use each containing the extract. The water-soluble ginger root extract of the present invention causes less skin irritation because of being substantially free of gingerols, and has excellent body-hair growth inhibiting effects, so that it is useful as a hair grown inhibitor and a preparation for external use, each having a high degree of safety.

17 Claims, 1 Drawing Sheet

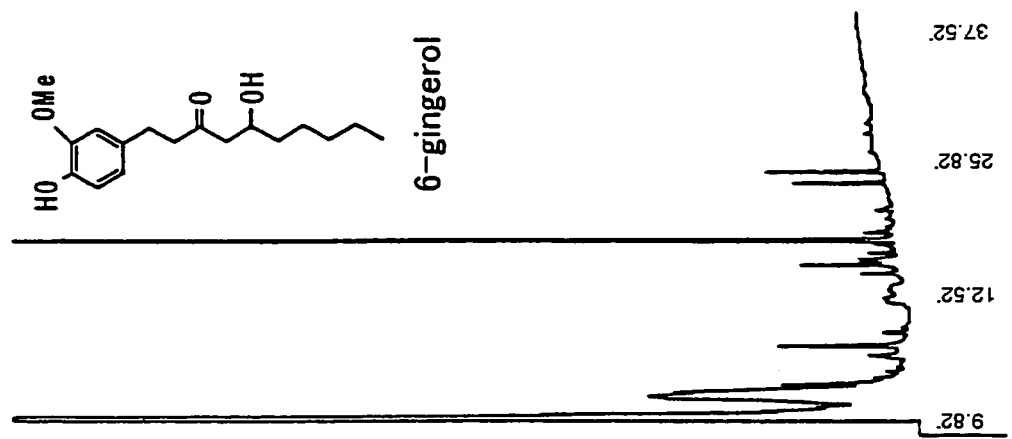
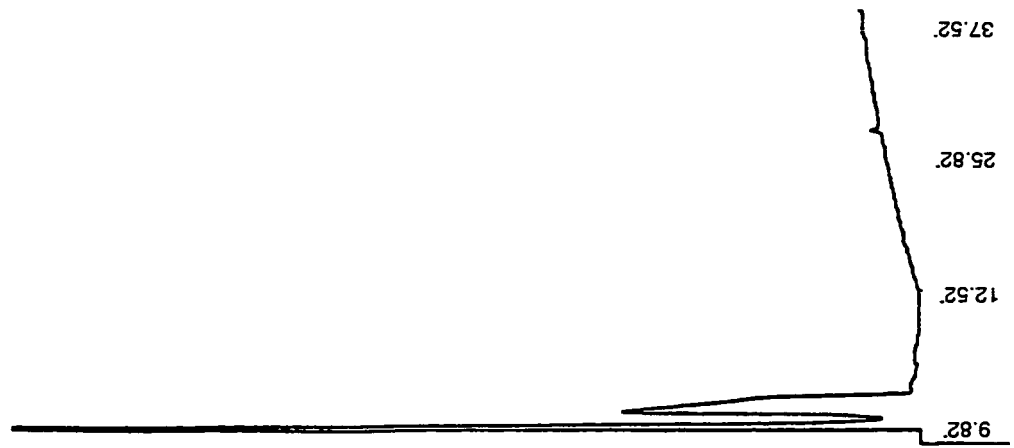

US 8,282,946 B2

WATER-SOLUBLE GINGER ROOT EXTRACT

This application is a divisional of U.S. application Ser. No. 10/209,858 (now abandoned), filed on Aug. 2, 2002, which claims priority to JP 2001-236854, filed on Aug. 3, 2001.

BACKGROUND OF THE INVENTION

1. Field of the Invention

The present invention relates to a water-soluble ginger root extract substantially free of gingerols.

2. Description of the related art

A ginger root is a root of *Zingiber officinale* Roscoe belonging to the Zingiberaceae plant family. It is a crude drug used for long years as a stomachic. The extract of this ginger root has also been used as a material for cosmetics because of its hair growth promoting and antipruritic actions. In "The Japanese Cosmetic Ingredients Codex", "ginger root extract" and "oil-soluble ginger root extract" are listed, while in "The Japanese Standards of Cosmetic Ingredients", "ginger root tincture" is listed.

As main ingredients of a ginger root, essential oil ingredients such as zingiberone and zingiberene, and pungent and stimulating ingredients such as gingerols (for example, 6-gingerol, 8-gingerol and 10-gingerol) are known. Because of its action derived from the latter ingredients, a ginger root has been incorporated in a hair tonic or the like to improve the blood flow. There is a report ("Natural Medicine, 40, 333-339 (1986)") that gingerols can satisfy the conditions as an indicator component of a ginger root. The existing "ginger root extract" and "oil-soluble ginger root extract" need a confirmation test by thin-layer chromatography, while the "ginger root tincture" needs "pungency" as its properties.

Gingerols have a strong skin irritating property so that an upper limit on their content is determined. "The Japanese Cosmetic Ingredients Codex" of Health and Welfare Ministry specifically limits the total amount of ginger root extract, oil soluble ginger root extract, ginger root tincture, capsicum tincture and cantharides tincture to 1% or less.

An object of the present invention is to provide a novel ginger root extract which is, different from the conventional one, substantially free of gingerols serving as a stimulant or pungent ingredient.

SUMMARY OF THE INVENTION

The present inventors have carried out various investigations on an extracting process of a ginger root. As a result, it has been found that a water-soluble ginger root extract substantially free of gingerols is available by subjecting a water extract or a hydrous alcohol extract of a ginger root to isolation and purification such as adsorption treatment; and that to their surprise, it is useful as a hair growth inhibitor or a preparation for external use (which will hereinafter be called "external preparation") owing to its action of suppressing the growth of body hairs.

In the present invention, there are thus provided a water-soluble ginger root extract which is a water or hydrous alcohol extract of a ginger root and is substantially free of gingerols; and a hair growth inhibitor and an external preparation each containing the extract.

The water-soluble ginger root extract of the invention causes less skin irritation because of being substantially free of gingerols, and has excellent body-hair growth inhibiting effects, so that it is useful as a hair grown inhibitor and an external preparation, each having a high degree of safety.

BRIEF DESCRIPTION OF THE DRAWING

FIG. 1 illustrates the results of componential analysis by HPLC (A: water-soluble ginger root extract (Example 1), B: ginger root extract (Comparative Example).

DETAILED DESCRIPTION OF THE EMBODIMENTS

The term "ginger root" as used herein means a root of *Zingiber officinale* Roscoe belonging to the Zingiberaceae plant family.

The term "substantially free of gingerols" means that the extract does not substantially contain gingerols such as 1-gingerol, 6-gingerol, 8-gingerol and 10-gingerol and in particular, the amount of 6-gingerol is not greater than 0.5 ppm, preferably not greater than a detection limit in HPLC analysis under the below-described conditions.

<HPLC Analysis Conditions>

Column: YMC-Pack ODS-A (4.6 mmΩ×150 mm)

Solvent: Solvent A: acetonitrile-water (30/70, v/v), Solvent B: acetonitrile

Gradient: Solvent A→(30 minutes)→Solvent B (maintained for 10 minutes)

Flow rate: 1.0 mL/min

Detection Wavelength: UV at 220 nm

The water-soluble ginger root extract according to the invention can be prepared, for example, by (a) extracting a ginger root with water or a hydrous alcohol and (b) subjecting the water-soluble extract solution to treatment with an adsorbent or liquid-liquid fractionation in a low-polarity solvent.

The above-described steps (a) and (b) will next be described specifically.

Step (a):

This step is for extracting a ginger root with water or a hydrous alcohol.

Here, as the raw material to be extracted, a ginger root cut into pieces or pulverized into powder is usable. A ginger root from which gingerols have been removed in advance, for example, a residue after removal of gingerols by extraction with a low-polarity solvent such as hexane, acetone or ethyl acetate or supercritical carbon dioxide is also usable.

As an extracting solvent, water or a hydrous alcohol is usable. Examples of the alcohol include ethanol, methanol, 1,3-butylene glycol and glycerin, of which ethanol and 1,3-butylene glycol are particularly preferred. The hydrous alcohol preferably has an alcohol concentration not greater than 70% (v/v). When the hydrous alcohol has an alcohol concentration exceeding 70%, a large amount of gingerols is mixed therein, which presumably disturbs smooth removal of gingerols.

To extraction, processes ordinarily employed for crude drugs can be applied. For example, the extract can be obtained by adding 5 to 30 parts by weight of water or the hydrous alcohol to 1 part by weight of the ginger root and then extracting the latter one with the former one while stirring at 5 to 60° C. for 0.5 hour to 3 days.

Step (b)

This step is for subjecting the extract solution obtained in the step (a) to treatment with an adsorbent or liquid-liquid fractionation in a low-polarity solvent, thereby obtaining the water-soluble ginger root extract of the invention.

The treatment with an adsorbent is, for example, a treatment to remove gingerols by adsorbing them to activated charcoal (powdered activated charcoal, granular activated charcoal, or the like) or to an aromatic adsorbent such as "Diaion HP20" (trade name; product of Mitsubishi Chemical Corp.) or "Amberlite XAD-2" or "Amberlite XAD-4" (trade name; product of Rohm & Haas Company).

The treatment with an adsorbent can be carried out by subjecting the extract solution to the treatment with about 0.1 to 15 wt. %, preferably about 0.4 to 5 wt. % of activated charcoal for 1 to 6 hours in a batch system and then removing the resulting adsorbent by filtration or centrifugal separation; or by filling a column with an adsorbent, causing the extract solution to pass through the column, thereby adsorbing gingerols to the adsorbent. Examples of the low-polarity solvent to be used for the liquid-liquid fractionation include hexane, ethyl acetate and petroleum ether.

This liquid-liquid fractionation can be achieved by adding the low-polarity solvent to the extract solution obtained in the step (a), bringing them in contact each other by agitation or stirring, separating the mixture into two layers by standing the mixture alone or centrifugal separation, and then removing the upper layer (organic layer) containing low-polarity ingredients such as 6-gingerol. If the mixture cannot be separated easily, it may be subjected to liquid-liquid fractionation after the extract solution is concentrated under reduced pressure to remove alcohols therefrom.

The treatment with an adsorbent or liquid-liquid fractionation in the step (b) may be followed by an ordinarily employed treatment such as filtration through a membrane filter as needed.

The componential analysis of the water-soluble ginger root extract by HPLC is shown in FIG. 1-A. It has revealed that different from the conventional ginger root extract (FIG. 1-B), it does not substantially contain pungent ingredients such as 6-gingerol.

As shown later in Examples, the water-soluble ginger root extract has a hair growth suppressing action. It can therefore be used as a drug or cosmetic, more specifically, a hair growth inhibitor or an external preparation without any further treatment or after diluting, concentrating or lyophilizing the extract and then grinding it into powder or paste.

The administration route of the hair growth inhibitor of the invention can be selected from transdermal administration, local intradermal administration and systemic administration, depending on the purpose of the administration or subject or site to be administered.

The hair growth suppressor or external preparation according to the invention, which is to be administered transdermally, preferably contains the water-soluble ginger root extract in an amount of 0.00001 to 10 wt. %, especially 0.0001 to 5 wt. % in terms of a solid content.

The hair growth suppressor or external preparation according to the invention is usable as pharmaceuticals, cosmetics or quasi-drugs. Use of it as hair-removing, depilatory, or shaving cosmetics or pharmaceuticals is especially preferred. Examples of such cosmetics or pharmaceuticals include hair removers in the form of paste, cream or aerosol, epilatories in the form of wax, gel and sheet, post-treatment lotions used after hair removal or depilation, anti-perspiration and deodorant cosmetics such as deodorant lotion, deodorant powder, deodorant spray and deodorant stick, cosmetics for use before shaving such as pre-shave lotion, shaving cosmetics such as shaving cream and cosmetics for use after shaving such as aftershave lotion.

The hair growth inhibitor or external preparation according to the invention may contain, in addition to the water-soluble ginger root extract, various ingredients ordinarily employed for pharmaceuticals, cosmetics or quasi-drugs, for example, purified water, ethanol, oily substance, humectant, thickener, antiseptic, emulsifier, medicinally effective ingredient, powder, ultraviolet absorber, colorant, perfume and emulsion stabilizer.

Examples of the medicinally effective ingredient include keratolytic agents and ingredients having a hair growth suppressing or depilating action such as thioglycolic acid and salts thereof. Examples of the keratolytic agents include lactic acid, BIOPRASE (trade mark, an alkaline proteinase from *Bacillus subtillis*, product of Nagase ChemteX Corp.), salicylic acid, glycolic acid, citric acid and malic acid, while examples of the salts of thioglycolic acid include sodium thioglycolate, potassium thioglycolate, ammonium thioglycolate and alkanolamine salts such as monoethanclamine thioglycolate, diethanolamine thioglycolate and triethanolamine thioglycolate. The keratolytic agent, or thioglycolic acid or salt thereof is added preferably in an amount of 0.01 to 10 wt. %, especially 0.05 to 5%.

EXAMPLES

Example 1

At room temperature, 200 g of a commercially available ginger root (product of Tochimoto Tenkaido Co., Ltd.) was extracted with a 200 (v/v) aqueous ethanol solution for 7 days, whereby an extract solution was obtained. To the extract solution, 10.0 g of activated charcoal ("Shirasagi P", product of Takeda Chemical Industries, Ltd.) was added. After stirring at room temperature for 2 hours, the mixture was filtered through a membrane filter and the filtrate was concentrated at 40° C. under reduced pressure. The residue was dissolved in 1 L of a 20% (v/v) aqueous ethanol solution, whereby 1 L of an extract was obtained (solid content: 2.4%).

Example 2

At room temperature, 20 g of a commercially available ginger root (product of Tochimoto Tenkaido Co., Ltd.) was extracted with 500 mL of acetone for 7 days. After removal of acetone from the extract, the residue was extracted further with 100 mL of a 20% (v/v) aqueous ethanol solution for 7 days at room temperature. The extract was filtered to obtain 80 mL of an extract solution. To the resulting extract solution was added 1.0 g of activated charcoal ("Shirasagi P", product of Takeda Chemical Industries, Ltd.). After stirring at room temperature for 2 hours, the mixture was filtered through a membrane filter, whereby 70 mL of an extract was obtained (solid content: 2.3%).

Example 3

Under the conditions of 21 MPa and 40° C., 20 g of a commercially available ginger root (product of Tochimoto Tenkaido Co., Ltd.) was extracted with 2 kg of supercritical carbon dioxide. The residue was extracted 5 further with 100 mL of a 200 (v/v) aqueous ethanol solution for 7 days at room temperature, followed by filtration, whereby 80 mL of an extract solution was obtained. To the resulting extract solution was added 0.8 g of activated charcoal ("Shirasagi P", product of Takeda Chemical Industries, Ltd.). After stirring at room temperature for 2 hours, the mixture was filtered through a membrane filter, whereby 75 mL of an extract was obtained (solid content: 2.1%).

Example 4

At room temperature, 20 g of a commercially available ginger root (product of Tochimoto Tenkaido Co., Ltd.) was extracted with 100 mL of a 50% (v/v) aqueous 1,3-butylene glycol solution for 7 days, followed by filtration, whereby 72 mL of an extract solution was obtained. To the resulting extract solution was added 1.0 g of activated charcoal ("Shirasagi P", product of Takeda Chemical Industries, Ltd.). After stirring at room temperature for 2 hours, the mixture was filtered through a membrane filter, whereby 65 mL of an extract was obtained (residue on evaporation: 2.0%).

Example 5

At room temperature, 20 g of a commercially available ginger root (product of Tochimoto Tenkaido Co., Ltd.) was extracted with 100 mL of a 50% (v/v) aqueous ethanol solution for 7 days, whereby 70 mL of an extract solution was obtained. After the extract solution was concentrated under reduced pressure at 40° C. to distill off ethanol, the residue was subjected to liquid-liquid fractionation with 100 mL of water and 200 mL of ethyl acetate, whereby a lower layer (water layer) was obtained. The water layer was concentrated under reduced pressure and the concentrate was then dissolved in a 20% (v/v) aqueous ethanol solution, whereby an extract was obtained (solid content: 1.8%).

Example 6

At room temperature, 20 g of a commercially available ginger root (product of Tochimoto Tenkaido Co., Ltd.) was extracted with 100 mL of a 70% (v/v) aqueous 1,3-butylene glycol solution for 7 days, followed by filtration, whereby 70 mL of an extract solution was obtained. To the resulting extract solution was added 1.0 g of activated charcoal ("Shirasagi P", product of Takeda Chemical Industries, Ltd.). After stirring at room temperature for 2 hours, the mixture was filtered through a membrane filter, whereby 60 mL of an extract was obtained (residue on evaporation: 1.8%).

Comparative Example

Preparation was conducted in accordance with the preparation process of a ginger root tincture as described in "The Japanese Standards of Cosmetic Ingredients". A commercially available ginger root (product of Tochimoto Tenkaido Co., Ltd., 200 g) was extracted with 1 L of a 74% (v/v) aqueous ethanol solution, followed by filtration, whereby an extract solution was obtained. The same aqueous ethanol solution was added to the extract to give the amount of 1 L, whereby an extract was obtained (solid content: 2.7%).

Test 1: Assay of 6-gingerol in Samples

To 2 mL of each of the samples weighed accurately, acetonitrile-water (30/70, v/v) was added to bring the volume to 10 mL, whereby a test solution was prepared. 10 µL of the test solution weighed accurately was assayed by HPLC under the below-described conditions. A calibration curve was drawn in a manner known per se in the art by using 6-gingerol (reference standard for crude drug test, product of Wako Pure Chemical Industries, Ltd.). The results are shown in Table 1.

<HPLC Analysis Conditions>
Column: YMC-Pack ODS-A (4.6 mmΩ×150 mm)
Solvent: Solvent A: acetonitrile-water (30/70, v/v), Solvent B: acetonitrile
Gradient: Solvent A→(30 minutes)→Solvent B (maintained for 10 minutes)
Flow rate: 1.0 mL/min
Detection wavelength: UV at 220 nm

TABLE 1

| | Concentration of 6-gingerol |
|---|---|
| Comparative Example | 380 ppm |
| Example 1 | Not detected |
| Example 2 | Not detected |
| Example 3 | Not detected |
| Example 4 | Not detected |
| Example 5 | Not detected |
| Example 6 | Not detected |

Test 2: Hair Growth Suppressing Effects

Each of the extract solutions obtained in Example 1 and Comparative Example was dissolved in 80% ethanol to give the final concentration of 1%, whereby a hair growth inhibitor was prepared. The back of 49-day-old C3H/HeNCrj mice, one group consisting of 20 mice, was shaved by an electric clippers and a hair removing cream with a care so as not to injure their skin. From the next day, the sample was applied to the shaved site by mL/twice/day for 4 weeks, while only the solvent was applied to a control group. In order to observe hair regrowth, the picture of the shaved site was taken at a fixed magnification and the day-dependent change of the area ratio of the regrowth hair (regrowth hair area/shaved area) was measured by an image analyzer.

As a result, apparent from Table 2, it has been found that the hair growth inhibitor containing the ginger root extract according to the invention exhibited an excellent hair growth inhibitory action. On the other hand, the extract of Comparative Example prepared in accordance with the existing preparation process of a ginger root tincture exhibited even a hair growth promoting action.

TABLE 2

| Test substance | Hair regrowth inhibition ratio (%) 3 weeks after shaving |
|---|---|
| Example 1 | 70.3 |
| Comparative Example | −5.0 |

What is claimed is:

1. A method of inhibiting hair growth comprising contacting the area for which hair growth inhibition is desired in a subject in need thereof with an external preparation comprising a water-soluble ginger root extract which comprises a water extract or a hydrous alcohol extract of a ginger root and which is substantially free of gingerols, wherein said hydrous alcohol extract of a ginger root has a maximum alcohol content of 70% v/v.

2. The method of claim 1, wherein said ginger root is the root of *Zingiber officinale* Roscoe.

3. The method of claim 1, wherein the concentration of 6-gingerol in said external preparation is 0.5 ppm or less.

4. The method of claim 1, wherein said external preparation further comprises an additional pharmaceutical, cosmetic or drug ingredient.

5. The method of claim 1, wherein the water-soluble ginger root extract is in an amount of 0.00001 to 10 wt % in terms of solid content.

6. The method of claim 1, wherein the external preparation is in a form selected from the group consisting of a paste, a cream, an aerosol, a wax, a gel, a sheet, a lotion, an antiperspiration and a deodorant cosmetic.

7. The method of claim 1, wherein the external composition further comprises one or more members selected from the group consisting of purified water, ethanol, an oily substance, a humectant, a thickener, an antiseptic, an emulsifier, a powder, an ultraviolet absorber, a colorant, a perfume and an emulsion stabilizer.

8. The method of claim 1, wherein the external composition further comprises one or more medicinally effective ingredients.

9. The method of claim 8, wherein the medicinally effective ingredient is selected from the group consisting of lactic acid, an alkaline proteinase from *Bacillus subtillis*, salicylic acid, glycolic acid, citric acid, malic acid, sodium thioglycolate, potassium thioglycolate, ammonium thioglycolate, monoethanolamine thioglycolate, diethanolamine thioglycolate, triethanolamine thioglycolate and mixtures thereof.

10. The method of claim 1, wherein said water-soluble ginger root extract is obtained by:
  (a) extracting the ginger root with water or a hydrous alcohol to form a water-soluble extract, and
  (b) treating the water soluble extract with an adsorbent or liquid-liquid fractionation in a low-polarity solvent.

11. The method of claim 10, wherein the alcohol is selected from ethanol, methanol, 1,3-butylene glycol or glycerin.

12. The method of claim 10, wherein the adsorbent is selected from activated charcoal, or an aromatic adsorbent.

13. The method of claim 10, wherein the low-polarity solvent is selected from hexane, ethyl acetate or petroleum ether.

14. The method of claim 10, wherein the liquid-liquid fractionation comprises
  (a) contacting the low-polarity solvent with the water-soluble extract by agitation or stirring to form a mixture,
  (b) separating the mixture into its respective organic and aqueous layers, and
  (c) removing the organic layer containing low-polarity ingredients.

15. The method of claim 10, further comprising filtering the water-soluble extract and adsorbent, or the water-soluble extract and low-polarity solvent.

16. The method of claim 1, wherein the gingerols have been removed from ginger root by treatment with a low-polarity solvent prior to formation of the water-soluble ginger root extract.

17. The method of claim 1, wherein said hydrous alcohol extract of a ginger root has a maximum alcohol content of 20% v/v.

* * * * *